(12) United States Patent
Kakiuchi et al.

(10) Patent No.: US 11,485,715 B2
(45) Date of Patent: Nov. 1, 2022

(54) METHOD FOR PRODUCING N-(HYDROCARBON)ISOCYANURIC ACID

(71) Applicant: NISSAN CHEMICAL CORPORATION, Tokyo (JP)

(72) Inventors: Nobuyuki Kakiuchi, Toyama (JP); Tomohisa Utsunomiya, Toyama (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 17/434,803

(22) PCT Filed: Mar. 2, 2020

(86) PCT No.: PCT/JP2020/008705
§ 371 (c)(1),
(2) Date: Aug. 30, 2021

(87) PCT Pub. No.: WO2020/179735
PCT Pub. Date: Sep. 10, 2020

(65) Prior Publication Data
US 2022/0162175 A1    May 26, 2022

(30) Foreign Application Priority Data
Mar. 1, 2019    (JP) .............................. JP2019-037604

(51) Int. Cl.
*C07D 251/32*    (2006.01)

(52) U.S. Cl.
CPC .................... *C07D 251/32* (2013.01)

(58) Field of Classification Search
CPC .................................................. C07D 251/32
See application file for complete search history.

(56) References Cited

U.S. PATENT DOCUMENTS 7,332,266 B2 *   2/2008   Kishioka ............ C08G 73/0655
                                                  430/514

FOREIGN PATENT DOCUMENTS

| JP | S38-7988 | B1 | 6/1963 |
| JP | S39-12340 | B1 | 7/1964 |
| JP | S48-26023 | B1 | 8/1973 |
| WO | 32/086624 | A1 | 10/2002 |
| WO | 2013/035787 | A1 | 3/2013 |
| WO | 2017/208910 | A1 | 12/2017 |

OTHER PUBLICATIONS

May 26, 2020 International Search Report issued in International Patent Application No. PCT/JP2020/008705.
May 26, 2020 Written Opinion issued in International Patent Application No. PCT/JP2020/008705.
W.J. Close. "Anticonvulsant Drugs: Monosubstituted Isocyanurates". Journal of American Chemical Society, 1953, vol. 75, pp. 3617-3618.
Jean-Louis Havet et al. "Synthesis and N-Methylation of Tetrabutylammonium Isocyanurate". Tetrahedron Letters, 2003, vol. 44, pp. 4399-4402.
Hikaru Fujita et al. "Study of the Reactivities of Acid-Catalyzed O-Benzylating Reagents Based on Structural Isomers of 1,3,5-Triazine". The Journal of Organic Chemistry, 2015, vol. 80, pp. 11200-11205.
Dong Ri Zhang et al. "Synthesis and Characterization of a New Adhesion-Activator for Polymer Surface". International Journal of Adhesion & Adhesives, 2005, vol. 25, pp. 371-378.

* cited by examiner

*Primary Examiner* — Sun Jae Yoo
(74) *Attorney, Agent, or Firm* — Oliff PLC

(57) ABSTRACT

A novel production method enables selective production of an isocyanuric acid N-substituted product of interest in one pot, requiring neither multiple steps nor cumbersome treatment, the method producing an N-(hydrocarbon)isocyanuric acid which includes a step N for reacting, in a solvent, a dihalogenated isocyanuric acid derivative with at least one hydrocarbonization agent selected from the group consisting of a halogenated hydrocarbon compound, a pseudo-halogenated hydrocarbon compound, and a dialkyl sulfate compound.

20 Claims, No Drawings

METHOD FOR PRODUCING N-(HYDROCARBON)ISOCYANURIC ACID

TECHNICAL FIELD

The present invention relates to a novel method for producing an N-(hydrocarbon)isocyanuric acid.

BACKGROUND ART

An N-substituted product of isocyanuric acid (hereinafter referred to as "isocyanuric acid N-substituted product") has been used in a variety of fields including semiconductor fields (e.g., Patent Documents 1 and 2), and various synthesis methods for the isocyanuric acid N-substituted product have been reported for many years (e.g., Non-Patent Documents 1 to 3).

Under such circumstances, the present inventors have hitherto reported a method for producing an isocyanuric acid N-substituted product having one hydrocarbon group (Patent Document 3).

PRIOR ART DOCUMENTS

Patent Documents

Patent Document 1: International Publication WO 02/086624
Patent Document 2: International Publication WO 2013/035787
Patent Document 3: International Publication WO 2017/208910

Non-Patent Documents

Non-Patent Document 1: Journal of American Chemical Society, 75, pp. 3617-3618 (1953)
Non-Patent Document 2: Tetrahedron Letters, 44, pp. 4399-4402 (2003)
Non-Patent Document 3: Journal of Organic Chemistry, 80, pp. 11200-11205 (2015)

SUMMARY OF THE INVENTION

Problems to be Solved by the Invention

A conventionally known production method for an isocyanuric acid N-substituted product having one alkyl group requires heating at a high temperature of 150° C. or higher for a long period of time, since isocyanuric acid has low solubility in an organic solvent. However, the production method is not industrially useful, since high-temperature reaction causes a reduction in yield due to decomposition of a raw material and a product, and sequential reaction causes, for example, a reduction in yield and selectivity. Also, the use of a reagent of low boiling point at a high temperature requires a closed type high-pressure reaction apparatus. Meanwhile, low-temperature reaction requires an excessively large amount of an organic solvent for dissolution of isocyanuric acid, which causes problems in terms of poor volume efficiency and an increase in the amount of waste liquid.

The method described in Patent Document 3, which has been provided for solving such problems, requires multiple reaction steps, and has room for improvement from the viewpoints of, for example, cost reduction and time savings.

An object of the present invention is to provide a method for producing an isocyanuric acid N-substituted product suitable for industrial production. Specifically, an object of the present invention is to provide an industrially superior novel production method which requires neither multiple steps nor cumbersome treatment, and which enables selective production of an isocyanuric acid N-substituted product of interest in one pot.

Means for Solving the Problems

The present inventors have conducted extensive studies for solving the aforementioned problems, and as a result have found that an N-mono(hydrocarbon)isocyanuric acid (i.e., mono-substituted product) or an N-di(hydrocarbon) isocyanuric acid (i.e., di-substituted product) can be selectively produced at room temperature in one pot by reacting, in a solvent, at least one dihalogenated isocyanuric acid derivative selected from the group consisting of a dihalogenated isocyanuric acid, a dihalogenated isocyanuric acid salt, and a dihalogenated isocyanuric acid salt hydrate with a hydrocarbonization agent, such as at least one alkylating agent selected from the group consisting of a halogenated hydrocarbon compound, a pseudo-halogenated hydrocarbon compound, and a dialkyl sulfate compound, preferably by mixing a solution or dispersion of a dihalogenated isocyanuric acid derivative with a hydrocarbonization agent such as a hydrocarbon-group-introducing alkylating agent, and controlling the amount of a present base during the mixing, or by mixing a solution or dispersion of a hydrocarbonization agent such as a hydrocarbon-group-introducing alkylating agent with a dihalogenated isocyanuric acid derivative, and controlling the amount of a present base during the mixing, more preferably by mixing an aqueous solution or aqueous dispersion of a dihalogenated isocyanuric acid derivative with a hydrocarbonization agent such as a hydrocarbon-group-introducing alkylating agent, and controlling the amount of a present base during the mixing. The present invention has been accomplished on the basis of this finding.

Accordingly, a first aspect of the present invention is a method for producing an N-(hydrocarbon)isocyanuric acid, the method comprising a step N of reacting, in a solvent, at least one dihalogenated isocyanuric acid derivative selected from the group consisting of a dihalogenated isocyanuric acid, a dihalogenated isocyanuric acid salt, and a dihalogenated isocyanuric acid salt hydrate with at least one hydrocarbonization agent selected from the group consisting of a halogenated hydrocarbon compound, a pseudo-halogenated hydrocarbon compound, and a dialkyl sulfate compound.

A second aspect of the present invention is the method for producing an N-(hydrocarbon)isocyanuric acid according to the first aspect, wherein the step N comprises a step X of providing a solution or dispersion of at least one dihalogenated isocyanuric acid derivative selected from the group consisting of a dihalogenated isocyanuric acid, a dihalogenated isocyanuric acid salt, and a dihalogenated isocyanuric acid salt hydrate, and a step Y of mixing the solution or dispersion of the dihalogenated isocyanuric acid derivative with at least one hydrocarbonization agent selected from the group consisting of a halogenated hydrocarbon compound, a pseudo-halogenated hydrocarbon compound, and a dialkyl sulfate compound, or comprises a step S of providing a solution or dispersion of at least one hydrocarbonization agent selected from the group consisting of a halogenated hydrocarbon compound, a pseudo-halogenated hydrocarbon compound, and a dialkyl sulfate compound, and a step T of mixing the solution or dispersion of the hydrocarbonization agent with at least one dihalogenated isocyanuric acid derivative selected from the group consisting of a dihalogenated isocyanuric acid, a dihalogenated isocyanuric acid salt, and a dihalogenated isocyanuric acid salt hydrate.

A third aspect of the present invention is the method for producing an N-(hydrocarbon)isocyanuric acid according to the second aspect, wherein the solution or dispersion of the dihalogenated isocyanuric acid derivative is an aqueous solution or an aqueous dispersion.

A fourth aspect of the present invention is the method for producing an N-(hydrocarbon)isocyanuric acid according to the third aspect, wherein the aqueous solution or aqueous dispersion of the dihalogenated isocyanuric acid derivative contains water.

A fifth aspect of the present invention is the method for producing an N-(hydrocarbon)isocyanuric acid according to any one of the second to fourth aspects, wherein the step Y is a step of mixing the solution or dispersion of the dihalogenated isocyanuric acid derivative with at least one hydrocarbonization agent selected from the group consisting of a halogenated hydrocarbon compound, a pseudo-halogenated hydrocarbon compound, and a dialkyl sulfate compound, and with a surfactant.

A sixth aspect of the present invention is the method for producing an N-(hydrocarbon)isocyanuric acid according to the fifth aspect, wherein the surfactant contains at least one selected from the group consisting of a quaternary ammonium salt, a crown ether, and an alkylbenzenesulfonic acid salt.

A seventh aspect of the present invention is the method for producing an N-(hydrocarbon)isocyanuric acid according to any one of the second to sixth aspects, wherein the step X is a step of providing a solution or dispersion containing at least one dihalogenated isocyanuric acid derivative selected from the group consisting of a dihalogenated isocyanuric acid, a dihalogenated isocyanuric acid salt, and a dihalogenated isocyanuric acid salt hydrate, and a base.

An eighth aspect of the present invention is the method for producing an N-(hydrocarbon)isocyanuric acid according to the seventh aspect, wherein the base contains an inorganic base.

A ninth aspect of the present invention is the method for producing an N-(hydrocarbon)isocyanuric acid according to the second aspect, wherein the solution or dispersion of the hydrocarbonization agent is an aqueous solution or an aqueous dispersion.

A tenth aspect of the present invention is the method for producing an N-(hydrocarbon)isocyanuric acid according to the ninth aspect, wherein the aqueous solution or aqueous dispersion of the hydrocarbonization agent contains water.

An eleventh aspect of the present invention is the method for producing an N-(hydrocarbon)isocyanuric acid according to any one of the second, ninth, or tenth aspect, wherein the step S is a step of providing a solution or dispersion containing at least one hydrocarbonization agent selected from the group consisting of a halogenated hydrocarbon compound, a pseudo-halogenated hydrocarbon compound, and a dialkyl sulfate compound, and a surfactant.

A twelfth aspect of the present invention is the method for producing an N-(hydrocarbon)isocyanuric acid according to the eleventh aspect, wherein the surfactant contains at least one selected from the group consisting of a quaternary ammonium salt, a crown ether, and an alkylbenzenesulfonic acid salt.

A thirteenth aspect of the present invention is the method for producing an N-(hydrocarbon)isocyanuric acid according to any one of the second and ninth to twelfth aspects, wherein the step S is a step of providing a solution or dispersion containing at least one hydrocarbonization agent selected from the group consisting of a halogenated hydrocarbon compound, a pseudo-halogenated hydrocarbon compound, and a dialkyl sulfate compound, and a base.

A fourteenth aspect of the present invention is the method for producing an N-(hydrocarbon)isocyanuric acid according to the thirteenth aspect, wherein the base contains an inorganic base.

A fifteenth aspect of the present invention is the method for producing an N-(hydrocarbon)isocyanuric acid according to any one of the first to fourteenth aspects, wherein the hydrocarbonization agent contains at least one selected from the group consisting of methyl p-toluenesulfonate, ethyl p-toluenesulfonate, methyl methanesulfonate, ethyl methanesulfonate, dimethyl sulfate, and diethyl sulfate.

A sixteenth aspect of the present invention is the method for producing an N-(hydrocarbon)isocyanuric acid according to the fifteenth aspect, wherein the hydrocarbonization agent contains at least one selected from the group consisting of dimethyl sulfate and diethyl sulfate.

A seventeenth aspect of the present invention is the method for producing an N-(hydrocarbon)isocyanuric acid according to any one of the first to sixteenth aspects, wherein the dihalogenated isocyanuric acid derivative contains at least one selected from the group consisting of dichloroisocyanuric acid, sodium dichloroisocyanurate, and sodium dichloroisocyanurate dihydrate.

An eighteenth aspect of the present invention is the method for producing an N-(hydrocarbon)isocyanuric acid according to the seventeenth aspect, wherein the dihalogenated isocyanuric acid derivative contains sodium dichloroisocyanurate.

A nineteenth aspect of the present invention is the method for producing an N-(hydrocarbon)isocyanuric acid according to any one of the first to eighteenth aspects, wherein the amount of the hydrocarbonization agent is 0.3 mole equivalent to 4.0 mole equivalent relative to 1 mole equivalent of the dihalogenated isocyanuric acid derivative.

A twentieth aspect of the present invention is the method for producing an N-(hydrocarbon)isocyanuric acid according to any one of the first to nineteenth aspects, wherein the amount of the dihalogenated isocyanuric acid derivative is 0.03 to 0.3 times by mass that of the solvent used.

Effects of the Invention

The present invention can provide an industrially useful production method which requires neither multiple steps nor cumbersome treatment, and which enables selective production of an N-(hydrocarbon)isocyanuric acid at room temperature in one pot with an eye on mass production.

MODES FOR CARRYING OUT THE INVENTION

The present invention is directed to a method for producing an N-(hydrocarbon)isocyanuric acid, the method including a step N of reacting, in a solvent, at least one dihalogenated isocyanuric acid derivative selected from the group consisting of a dihalogenated isocyanuric acid, a dihalogenated isocyanuric acid salt, and a dihalogenated isocyanuric acid salt hydrate with at least one hydrocarbonization agent selected from the group consisting of a halogenated hydrocarbon compound, a pseudo-halogenated hydrocarbon compound, and a dialkyl sulfate compound.

Preferably, in the present invention, the step N includes a step X of providing a solution or dispersion of at least one dihalogenated isocyanuric acid derivative selected from the group consisting of a dihalogenated isocyanuric acid, a dihalogenated isocyanuric acid salt, and a dihalogenated isocyanuric acid salt hydrate, and a step Y of mixing the solution or dispersion of the dihalogenated isocyanuric acid derivative with at least one hydrocarbonization agent selected from the group consisting of a halogenated hydrocarbon compound, a pseudo-halogenated hydrocarbon compound, and a dialkyl sulfate compound, or includes a step S of providing a solution or dispersion of at least one hydrocarbonization agent selected from the group consisting of a halogenated hydrocarbon compound, a pseudo-halogenated hydrocarbon compound, and a dialkyl sulfate compound, and a step T of mixing the solution or dispersion of the hydrocarbonization agent with at least one dihalogenated isocyanuric acid derivative selected from the group consisting of a dihalogenated isocyanuric acid, a dihalogenated isocyanuric acid salt, and a dihalogenated isocyanuric acid salt hydrate.

More preferably, in the present invention, the solution or dispersion of the aforementioned dihalogenated isocyanuric acid derivative or hydrocarbonization agent is an aqueous solution or an aqueous dispersion.

Thus, in a more preferred embodiment of the present invention, the step N includes a step A of providing an aqueous solution or aqueous dispersion of at least one dihalogenated isocyanuric acid derivative selected from the group consisting of a dihalogenated isocyanuric acid, a dihalogenated isocyanuric acid salt, and a dihalogenated isocyanuric acid salt hydrate, and a step B of mixing the aqueous solution or the aqueous dispersion with a hydrocarbonization agent such as an alkylating agent. In a still more preferred embodiment, the step A is a step A1 of providing an aqueous solution of at least one dihalogenated isocyanuric acid derivative selected from the group consisting of a dihalogenated isocyanuric acid, a dihalogenated isocyanuric acid salt, and a dihalogenated isocyanuric acid salt hydrate.

The N-(hydrocarbon)isocyanuric acid according to the present invention refers to an isocyanuric acid (N-substituted product) having one or two hydrocarbon groups; specifically, a compound of the following Formula (1) (N-mono(hydrocarbon)isocyanuric acid) wherein one hydrocarbon group (substituent) is bonded to a nitrogen atom of isocyanuric acid, or a compound of the following Formula (2) (N-di(hydrocarbon)isocyanuric acid) wherein two hydrocarbon groups (substituents) are bonded to nitrogen atoms of isocyanuric acid.

In Formula (1) or (2), R is, for example, a $C_{1-10}$ hydrocarbon group. The hydrocarbon group may be linear, branched, or cyclic, and may have at least one double bond or triple bond. When the hydrocarbon group is an alkyl group, the alkyl group is, for example, any of methyl group, ethyl group, n-propyl group, isopropyl group, n-butyl group, isobutyl group, n-pentyl group, n-hexyl group, n-heptyl group, n-octyl group, n pentyl group, n nonyl group, n-decyl group, cyclohexylmethyl group, and cyclopentylmethyl group. Examples of the hydrocarbon group other than the alkyl group include benzyl group, allyl group, and propargyl group.

In Formula (2), Rs may be identical to or different from each other. Preferably, Rs are identical to each other from the viewpoint of efficient production of a target product.

The respective steps of the method of the present invention will next be described.

(1) Step N of Reacting Dihalogenated Isocyanuric Acid Derivative with Hydrocarbonization Agent in Solvent This step involves reacting a dihalogenated isocyanuric acid derivative (i.e., starting material) with a hydrocarbonization agent in a solvent.

In the present invention, the aforementioned dihalogenated isocyanuric acid derivative refers to a dihalogenated isocyanuric acid, a dihalogenated isocyanuric acid salt, or a dihalogenated isocyanuric acid salt hydrate. These dihalogenated isocyanuric acid derivatives may be used alone or in combination of two or more species. Preferably, a single dihalogenated isocyanuric acid derivative is used, from the viewpoint of efficient production of a target product.

The dihalogenated isocyanuric acid may be, for example, a compound of the following Formula (3); the dihalogenated isocyanuric acid salt may be, for example, a compound of the following Formula (4); and the dihalogenated isocyanuric acid salt hydrate may be, for example, a compound of the following Formula (5). Tautomers are shown in each of the following Formulae (3) to (5).

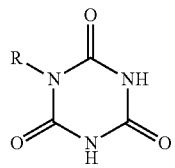

(1)

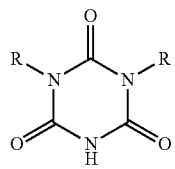

(2)

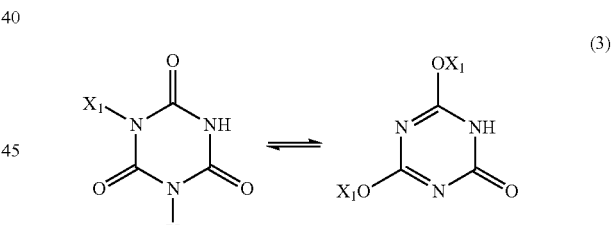

(3)

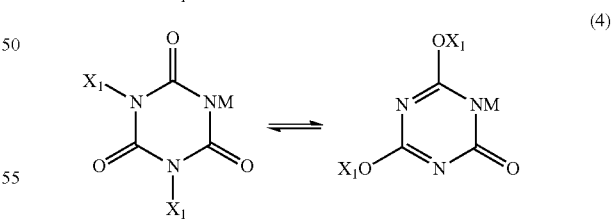

(4)

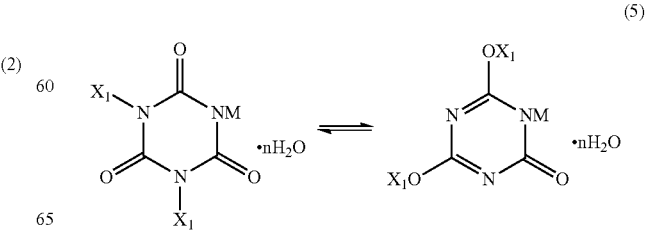

(5)

In Formulae (3), (4), and (5), $X_1$ is a halogen atom and may be selected from among an iodine atom, a bromine atom, a chlorine atom, and a fluorine atom. In each of Formulae (3), (4), and (5), $X_1$s may be identical to or different from each other.

M is an alkali metal and may be selected from among, for example, lithium, sodium, and potassium, and n is the number of hydrated water molecules.

In the present invention, the aforementioned dihalogenated isocyanuric acid derivatives of each type may be used alone or in combination of two or more species, and/or the dihalogenated isocyanuric acid derivatives of different types may be used in combination of two or more species. Preferably, a single derivative is used, from the viewpoint of efficient production of a target product.

Among the dihalogenated isocyanuric acid derivatives of Formulae (3), (4), and (5), dichloroisocyanuric acid, sodium dichloroisocyanurate, or sodium dichloroisocyanurate dihydrate is preferably used, from the viewpoint of industrial advantages, such as good solubility in water, etc., easy availability, and inexpensiveness.

The aforementioned dihalogenated isocyanuric acid derivative may be a commercially available product, or may be synthesized by, for example, any known method.

The dihalogenated isocyanuric acid derivative (e.g., dichloroisocyanuric acid derivative) synthesized by, for example, any known method may be used after isolation. Alternatively, a reaction mixture containing the dihalogenated isocyanuric acid derivative may be used, as is, in the present invention without isolation.

For example, isocyanuric acid may be reacted with a halogenating agent (e.g., sodium hypochlorite or chlorine) in a solvent, and the resultant reaction mixture containing one or more selected from among dichloroisocyanuric acid, sodium dichloroisocyanurate, and sodium dichloroisocyanurate dihydrate may be mixed with a hydrocarbonization agent described below.

No particular limitation is imposed on the aforementioned solvent, so long as it is used in this type of reaction and does not adversely affect the reaction. Water, a buffer, and a water-soluble organic solvent are preferably used, from the viewpoints of, for example, production of a target product with high reproducibility, production of a target product at high yield, and workability. A single solvent may be used, or two or more solvents may be used in combination.

From the aforementioned viewpoints, the solvent used can be selected from among water, a buffer, and a water-soluble organic solvent.

No particular limitation is imposed on the aforementioned water. For example, industrial tap water, clean tap water, surface water, underground water, or well water may be used without limitation, or ion-exchange water, distilled water, RO water, etc. may be used.

The aforementioned buffer may be any known buffer depending on the target pH. Examples of the buffer include buffers having buffering ability in a neutral region or a neutral to basic region, such as phosphate (e.g., disodium hydrogen phosphate, sodium dihydrogen phosphate, potassium phosphate, trisodium phosphate, and a mixture of any of these) buffer, ammonium formate buffer, and ammonium acetate buffer.

Examples of the aforementioned water-soluble organic solvent (hydrophilic solvent) include, but are not limited to, alcohols, such as methanol, ethanol, n-propanol, isopropyl alcohol, n-butanol, isobutyl alcohol, and 2-methoxypropanol; glycols, such as ethyl cellosolve, butyl cellosolve, ethylene glycol, and diethylene glycol; glycol ethers, such as propylene glycol monomethyl ether; ethers, such as tetrahydrofuran (THF); ketones, such as acetone; nitriles, such as acetonitrile; cyclic amides, such as N,N-dimethylformamide (DMF), N,N-dimethylacetamide (DMAc), and N-methyl-2-pyrrolidone (NMP); and sulfoxides, such as dimethyl sulfoxide (DMSO). These water-soluble organic solvents may be used alone or in combination of two or more species.

The aforementioned water-soluble organic solvent may be used in the form of a mixed solvent with water. In such a case, no particular limitation is imposed on the mixing ratio of water to the water-soluble organic solvent, so long as a homogeneous system can be maintained, for example, during provision (preparation) of an aqueous solution (aqueous dispersion) and after addition of a hydrocarbonization agent such as an alkylating agent described below. The mixing ratio (by mass) of water to the water-soluble organic solvent is, for example, 0.1:99.9 to 99.9:0.1.

The water-soluble organic solvent may be used in combination with a slightly water-soluble organic solvent or a hydrophobic organic solvent (e.g., propylene glycol 1-monomethyl ether 2-acetate (PGMEA)), so long as the effects of the present invention are not impaired.

The hydrocarbonization agent (e.g., alkylating agent), such as the aforementioned halogenated hydrocarbon compound, pseudo-halogenated hydrocarbon compound, or dialkyl sulfate compound, is used for the purpose of introduction of a hydrocarbon group (e.g., alkyl group). In the present specification, a halogenated hydrocarbon compound, a pseudo-halogenated hydrocarbon compound, and a dialkyl sulfate compound may be collectively referred to as "hydrocarbonization agent."

The halogenated hydrocarbon compound or the pseudo-halogenated hydrocarbon compound may be, for example, a compound of the following Formula (6).

  (6)

In Formula (6), R is a $C_{1-10}$ hydrocarbon group as shown in Formulae (1) and (2). The hydrocarbon group may be linear, branched, or cyclic, and may have at least one double bond or triple bond.

$X_2$ is a halogen atom or a pseudo-halogen group.

The aforementioned halogen atom may be selected from among an iodine atom, a bromine atom, a chlorine atom, and a fluorine atom.

When $X_2$ is a halogen atom, the compound of Formula (6) is a halogenated hydrocarbon compound. Examples of the compound include, but are not limited to, methyl iodide, ethyl bromide, propyl bromide, allyl bromide, and propargyl bromide.

Examples of the aforementioned pseudo-halogen group include alkylsulfonyloxy groups, such as methanesulfonyloxy group; fluoroalkylsulfonyloxy groups, such as trifluoromethanesulfonyloxy group and nonafluorobutanesulfonyloxy group; and aromatic sulfonyloxy groups, such as benzenesulfonyloxy group and toluenesulfonyloxy group.

When $X_2$ is a pseudo-halogen group, the compound of Formula (6) is a pseudo-halogenated hydrocarbon compound. Examples of the compound include, but are not limited to, methyl p-toluenesulfonate, ethyl p-toluenesulfonate, methyl methanesulfonate, and ethyl methanesulfonate.

The aforementioned dialkyl sulfate compound may be, for example, a compound of the following Formula (7).

  (7)

In Formula (7), R is a $C_{1-10}$ hydrocarbon group as shown in Formulae (1) and (2). The hydrocarbon group may be linear, branched, or cyclic, and may have at least one double bond or triple bond. In Formula (7), two Rs may be identical to or different from each other. Preferably, Rs are identical to each other, from the viewpoint of efficient production of a target product.

Examples of the aforementioned dialkyl sulfate compound include dimethyl sulfate and diethyl sulfate.

No particular limitation is imposed on the amount of the aforementioned hydrocarbonization agent (at least one selected from the group consisting of a halogenated hydrocarbon compound, a pseudo-halogenated hydrocarbon compound, and a dialkyl sulfate compound) to be used, so long as the effects of the present invention are not impaired. Preferably, the amount of the hydrocarbonization agent used is 0.3 mole equivalent to 4.0 mole equivalent relative to 1 mole equivalent of the dihalogenated isocyanuric acid derivative.

No particular limitation is imposed on the amount of the aforementioned dihalogenated isocyanuric acid derivative, so long as the effects of the present invention are not impaired. The amount of the dihalogenated isocyanuric acid derivative is generally about 0.03 to 0.3 times by mass that of the solvent used.

No particular limitation is imposed on the reaction temperature, so long as the reaction proceeds. The reaction temperature may be appropriately determined in consideration of, for example, the solvent used, the amount of the dihalogenated isocyanuric acid derivative, and the type and amount of the hydrocarbonization agent. In a certain embodiment of the present invention, the reaction temperature is, for example, 0° C. to 70° C. The reaction temperature is preferably 10° C. to 40° C., more preferably around ambient temperature (20° C.±15° C.), from the viewpoints of, for example, efficient progress of the reaction, prevention of the decomposition or volatilization of a raw material used, and production of a target product with high reproducibility.

The aforementioned reaction may be performed in the presence of a base. The use of a base enables more selective production of an N-di(hydrocarbon)isocyanuric acid.

No particular limitation is imposed on the base, so long as it is used in this type of reaction and does not adversely affect the reaction. Preferably, an inorganic base is used. Examples of the inorganic base include alkali metal hydroxides, such as sodium hydroxide and potassium hydroxide; alkali metal carbonates, such as sodium carbonate and potassium carbonate; alkaline earth metal carbonates, such as calcium carbonate and magnesium carbonate; and alkali metal hydrogen carbonates, such as sodium hydrogen carbonate and potassium hydrogen carbonate. Of these, an alkali metal hydroxide is preferably used, and sodium hydroxide is particularly preferably used. These inorganic bases may be used alone or in combination of two or more species. The inorganic base used may be an anhydrate or a hydrate.

No particular limitation is imposed on the amount of the aforementioned base used, so long as the effects of the present invention are not impaired. The amount of the base used is preferably 0.5 mole equivalent to 3.0 mole equivalent relative to 1 mole equivalent of the dihalogenated isocyanuric acid derivative contained in the aforementioned solution (dispersion).

When such a base is used, the base may be mixed with and dissolved in a solvent during mixing of the aforementioned dihalogenated isocyanuric acid derivative with the solvent. Alternatively, the base may be added to and dissolved in the solvent before or after mixing of the dihalogenated isocyanuric acid derivative with the solvent.

No particular limitation is imposed on the temperature at mixing (addition) or dissolution of the base. Similar to the case of mixing or dissolution of the aforementioned dihalogenated isocyanuric acid derivative, the temperature may be appropriately adjusted (to, for example, room temperature (ambient temperature) to 50° C.) depending on the solubility of the base used.

The aforementioned reaction may be performed in the presence of a surfactant such as a phase transfer catalyst.

Examples of the surfactant serving as a phase transfer catalyst include quaternary ammonium salts, such as benzyltrimethylammonium chloride, benzyltriethylammonium chloride, tetramethylammonium chloride, tetra-n-butylammonium bromide, and tetra-n-butylammonium hydrogen sulfate; quaternary phosphonium salts, such as tetraphenylphosphonium bromide; crown ethers, such as 12-crown-4 and 18-crown-6; and alkylbenzenesulfonic acid salts, such as sodium dodecylbenzenesulfonate. Of these, a quaternary ammonium salt can be used as a preferred phase transfer catalyst. These phase transfer catalysts may be used alone or in combination of two or more species.

When the aforementioned surfactant (e.g., phase transfer catalyst) is used, no particular limitation is imposed on the amount of the surfactant, so long as the effects of the present invention are not impaired. The amount of the surfactant is generally 0.001 mole equivalent to 1.5 mole equivalent relative to 1 mole equivalent of the aforementioned dihalogenated isocyanuric acid derivative.

The aforementioned hydrocarbonization agent and an optionally used surfactant may optionally be dissolved or dispersed in a solvent, and may be used in the form of a solution or a dispersion.

The resultant target product can be isolated by a common method, and no particular limitation is imposed on the purification operation. For example, the solid precipitated after the reaction may be recovered through filtration, and the resultant solid may be washed with water or an aqueous solution of a reducing agent (e.g., sodium thiosulfate), followed by recrystallization in an organic solvent for an increase in purity. Alternatively, phase separation using an organic solvent may be performed.

The present invention will next be described in more detail, but the present invention is not limited to the following description. Thus, in a preferred embodiment, the aforementioned step N includes steps X and Y described below or steps S and T described below. In a more preferred embodiment, the step N includes steps A and B described below.

(2) Step X of Providing Solution or Dispersion of Dihalogenated Isocyanuric Acid Derivative, or Step A of Providing Aqueous Solution or Aqueous Dispersion of Dihalogenated Isocyanuric Acid Derivative This step involves providing a solution or dispersion of a dihalogenated isocyanuric acid derivative (i.e., starting material), or an aqueous solution or aqueous dispersion of the dihalogenated isocyanuric acid derivative; specifically, dissolving or dispersing the dihalogenated isocyanuric acid derivative in a solvent described below, to thereby provide (prepare) a solution or dispersion or aqueous solution or aqueous dispersion of the dihalogenated isocyanuric acid derivative used in the subsequent step B.

The definitions, specific examples, and other conditions of the dihalogenated isocyanuric acid derivative used in the present invention are the same as those described above.

No particular limitation is imposed on the solvent used for providing (preparing) the solution (dispersion), so long as it is used in this type of reaction and does not adversely affect the reaction. Water, a buffer, and a water-soluble organic solvent are preferably used, from the viewpoints of, for example, production of a target product with high reproducibility, production of a target product at high yield, and workability.

From the aforementioned viewpoints, the solvent used for providing (preparing) the aqueous solution (aqueous dispersion) can be selected from among water, a buffer, and a water-soluble organic solvent. Specific examples and other conditions of the water and the water-soluble organic solvent are the same as those described above.

For provision (preparation) of the solution (dispersion), one or more solvents may be mixed with the aforementioned dihalogenated isocyanuric acid derivative, to thereby dissolve the derivative in the solvents. For provision (preparation) of the solution (dispersion), one or more solvents may be mixed with isocyanuric acid and the aforementioned halogenating agent, to thereby provide (prepare) a reaction solvent containing the aforementioned dihalogenated isocyanuric acid derivative.

For provision (preparation) of the aqueous solution (aqueous dispersion), water, a buffer, or a water-soluble organic solvent, or a mixed solvent of water and a water-soluble organic solvent may be mixed with the aforementioned dihalogenated isocyanuric acid derivative, to thereby dissolve the derivative in, for example, water. For provision (preparation) of the aqueous solution (aqueous dispersion), water, a buffer, or a water-soluble organic solvent, or a mixed solvent of water or a buffer and a water-soluble organic solvent may be mixed with isocyanuric acid and the aforementioned halogenating agent, to thereby provide (prepare) a reaction aqueous solution containing the aforementioned dihalogenated isocyanuric acid derivative.

In such a case, no particular limitation is imposed on the temperature at mixing or dissolution, and the temperature may be appropriately determined depending on the solubility or dispersibility of the dihalogenated isocyanuric acid derivative or isocyanuric acid and the halogenating agent. The temperature may be, for example, around ambient temperature (20° C.±15° C.). Optionally, heating may be appropriately performed for dissolution. Since the dihalogenated isocyanuric acid derivative has high solubility in, for example, water, the aqueous solution can be generally provided (prepared) at room temperature (ambient temperature).

The solution (dispersion) or the aqueous solution (aqueous dispersion) may further contain a base. The reaction system containing a base enables more selective production of an N-di(hydrocarbon)isocyanuric acid in steps Y and B described below. Specific examples of the base are the same as those described above.

No particular limitation is imposed on the amount of the base used, so long as the effects of the present invention are not impaired. The amount of the base used is preferably 0.5 mole equivalent to 3.0 mole equivalent relative to 1 mole equivalent of the dihalogenated isocyanuric acid derivative contained in the aforementioned solution (dispersion) or aqueous solution (aqueous dispersion).

When a base is used, no particular limitation is imposed on the order of mixing (addition) and dissolution of the base. Specifically, the base may be mixed with and dissolved in a solvent, water, a buffer, a water-soluble organic solvent, or a mixed solvent of water or a buffer and a water-soluble organic solvent during mixing of the aforementioned dihalogenated isocyanuric acid derivative. Alternatively, the base may be added to and dissolved in such a solvent before or after mixing of the dihalogenated isocyanuric acid derivative. When a base is used, a basic buffer containing, for example, ammonium acetate, ammonium formate, or aqueous ammonia may be used.

No particular limitation is imposed on the temperature at mixing (addition) or dissolution of the base. Similar to the case of mixing or dissolution of the aforementioned dihalogenated isocyanuric acid derivative, the temperature may be appropriately adjusted (to, for example, room temperature (ambient temperature) to 50° C.) depending on the solubility of the base used.

In the present invention, the step Y or B may be performed even when the dihalogenated isocyanuric acid derivative and the base (if used) are in the form of a partially dissolved solution. However, from the viewpoints of, for example, production of a target product with high reproducibility, production of a target product at high yield, and workability, the step Y or B is preferably performed after confirmation that the dihalogenated isocyanuric acid derivative and the base (if used) are completely dissolved in a solvent to form a homogeneous solution.

(3) Step Y of Mixing Solution or Dispersion of Dihalogenated Isocyanuric Acid Derivative with at Least One Hydrocarbonization Agent Selected from the Group Consisting of Halogenated Hydrocarbon Compound, Pseudo-Halogenated Hydrocarbon Compound, and Dialkyl Sulfate Compound, or Step B of Mixing Aqueous Solution or Aqueous Dispersion of Dihalogenated Isocyanuric Acid Derivative with at Least One Hydrocarbonization Agent Selected from the Group Consisting of Halogenated Hydrocarbon Compound, Pseudo-Halogenated Hydrocarbon Compound, and Dialkyl Sulfate Compound This step involves mixing the solution (dispersion) or aqueous solution (aqueous dispersion) obtained in the aforementioned step X or A with at least one hydrocarbonization agent selected from the group consisting of a halogenated hydrocarbon compound, a pseudo-halogenated hydrocarbon compound, and a dialkyl sulfate compound.

The definitions, specific examples, and other conditions (e.g., amount to be used) of the hydrocarbonization agent, the halogenated hydrocarbon compound, the pseudo-halogenated hydrocarbon compound, and the dialkyl sulfate compound are the same as those described above.

In the step Y or B, a surfactant (e.g., phase transfer catalyst) may be used together with the aforementioned hydrocarbonization agent. Specific examples of the surfactant are the same as those described above.

When the surfactant (e.g., phase transfer catalyst) is used, no particular limitation is imposed on the amount of the surfactant used, so long as the effects of the present invention are not impaired. The amount of the surfactant is generally 0.001 mole equivalent to 1.5 mole equivalent relative to 1 mole equivalent of the dihalogenated isocyanuric acid derivative contained in the aforementioned solution (dispersion) or aqueous solution (aqueous dispersion).

The aforementioned hydrocarbonization agent (at least one selected from the group consisting of a halogenated hydrocarbon compound, a pseudo-halogenated hydrocarbon compound, and a dialkyl sulfate compound) and an optionally used surfactant may optionally be dissolved or dispersed in a solvent, and may be used in the form of a solution or a dispersion.

The solution (dispersion) or aqueous solution (aqueous dispersion) of the dihalogenated isocyanuric acid derivative provided in the aforementioned step X or A is mixed with the hydrocarbonization agent (at least one selected from the group consisting of a halogenated hydrocarbon compound, a pseudo-halogenated hydrocarbon compound, and a dialkyl sulfate compound) and an optionally used surfactant generally after the step X or A of providing the solution (dispersion) or aqueous solution (aqueous dispersion) of the dihalogenated isocyanuric acid derivative.

No limitation is imposed on this mixing method, so long as the solution (dispersion) or aqueous solution (aqueous dispersion) provided in the aforementioned step X or A is mixed with the hydrocarbonization agent and an optionally used surfactant.

Next will be described a method for mixing the aqueous solution (aqueous dispersion) provided in the step A with the hydrocarbonization agent (e.g., the aforementioned alkylating agent) and an optionally used surfactant.

Firstly, the hydrocarbonization agent (e.g., the aforementioned alkylating agent) and an optionally used surfactant are added to the aqueous solution (aqueous dispersion) provided in the step A without any treatment (e.g., without temperature adjustment). In this case, the aqueous solution (aqueous dispersion) provided in the step A may be added to the hydrocarbonization agent (e.g., alkylating agent) and an optionally used surfactant (without, for example, temperature adjustment).

After completion of this addition, the reaction of producing an N-(hydrocarbon)isocyanuric acid proceeds in the reaction system. In this case, when the aforementioned base is absent in the reaction system, an N-mono(hydrocarbon)isocyanuric acid is selectively produced, whereas when the aforementioned base is present in the reaction system, an N-di(hydrocarbon)isocyanuric acid is selectively produced. After completion of the addition, the production of an N-(hydrocarbon)isocyanuric acid can be promoted by stirring the reaction system.

After completion of the addition, the reaction temperature (the temperature in the reaction system) can be maintained at ambient temperature (20° C.±15° C.) following the aforementioned step A, and may be appropriately adjusted (to, for example, room temperature (ambient temperature) to 50° C.) in consideration of, for example, the degree of progress of the reaction or the recovery procedure after production of an N-(hydrocarbon)isocyanuric acid. The reaction of production of an N-(hydrocarbon)isocyanuric acid seems to proceed relatively easily even at room temperature (ambient temperature), and thus the reaction at room temperature (ambient temperature) is advantageous from the industrial viewpoint.

No particular limitation is imposed on the reaction time, so long as the effects of the present invention are not impaired. The reaction time may vary depending on the type of the hydrocarbonization agent (at least one selected from the group consisting of a halogenated hydrocarbon compound, a pseudo-halogenated hydrocarbon compound, and a dialkyl sulfate compound) to be used, the presence or absence of a surfactant, and the type of the surfactant, and the reaction time is, for example, 0.1 hours to 10 hours.

When the aforementioned hydrocarbonization agent (at least one selected from the group consisting of a halogenated hydrocarbon compound, a pseudo-halogenated hydrocarbon compound, and a dialkyl sulfate compound) is used in combination with a surfactant, no particular limitation is imposed on the order of addition (contact and mixing with the aqueous solution) of these materials. Preferably, the surfactant is first added (contacted and mixed with the aqueous solution), and then the hydrocarbonization agent is added, whereby the reaction can be caused to proceed uniformly.

No particular limitation is imposed on the purification operation. For example, the solid precipitated after the reaction may be recovered through filtration, and the resultant solid may be washed with water or an aqueous solution of a reducing agent (e.g., sodium thiosulfate), followed by recrystallization in an organic solvent or water and drying for an increase in purity. Alternatively, phase separation using an organic solvent may be performed.

(4) Step S of Providing Solution or Dispersion of at Least One Hydrocarbonization Agent Selected from the Group Consisting of Halogenated Hydrocarbon Compound, Pseudo-Halogenated Hydrocarbon Compound, and Dialkyl Sulfate Compound This step involves providing a solution (dispersion) or aqueous solution (aqueous dispersion) of a hydrocarbonization agent; specifically, dissolving or dispersing the hydrocarbonization agent in a solvent described above, to thereby provide (prepare) a solution, aqueous solution, or (aqueous) dispersion of the hydrocarbonization agent used in the subsequent step T.

The definitions, specific examples, and other conditions (e.g., amount to be used) of the hydrocarbonization agent used in the step S are the same as those described above.

No particular limitation is imposed on the solvent used for providing (preparing) the solution (dispersion), so long as it is used in this type of reaction and does not adversely affect the reaction. Water, a buffer, and a water-soluble organic solvent are preferably used, from the viewpoints of, for example, production of a target product with high reproducibility, production of a target product at high yield, and workability. Specific examples and other conditions of the water and the water-soluble organic solvent are the same as those described above.

For provision (preparation) of the solution (dispersion), one or more solvents may be mixed with the aforementioned hydrocarbonization agent, to thereby dissolve or disperse the hydrocarbonization agent in the solvents.

For provision (preparation) of the aqueous solution (aqueous dispersion), water, a buffer, or a water-soluble organic solvent, or a mixed solvent of water or a buffer and a water-soluble organic solvent may be mixed with the aforementioned hydrocarbonization agent, to thereby dissolve or disperse the hydrocarbonization agent in, for example, water.

In such a case, no particular limitation is imposed on the temperature at mixing, dissolution, or dispersion, and the temperature may be appropriately determined depending on the solubility or dispersibility of the hydrocarbonization agent. The temperature may be, for example, around ambient temperature (20° C.±15° C.).

The solution (dispersion) or the aqueous solution (aqueous dispersion) may contain a surfactant (e.g., phase transfer catalyst) together with the aforementioned hydrocarbonization agent. Specific examples and conditions (e.g., amount to be used) of the surfactant used are the same as those described above.

The solution (dispersion) or the aqueous solution (aqueous dispersion) may further contain a base. The reaction system containing a base enables more selective production of an N-di(hydrocarbon)isocyanuric acid in the step T described below. Specific examples and conditions (e.g., amount to be used) of the base are the same as those described above.

The aforementioned hydrocarbonization agent and optionally used surfactant and base may optionally be dissolved or dispersed in a solvent, and may be used in the form of a solution or a dispersion.

When a surfactant is used, no particular limitation is imposed on the order of mixing (addition), dissolution, and dispersion of the surfactant. Specifically, the surfactant may be mixed with and dissolved or dispersed in a solvent during mixing of the aforementioned hydrocarbonization agent. Alternatively, the surfactant may be added to and dissolved or dispersed in such a solvent before or after mixing of the hydrocarbonization agent.

No particular limitation is imposed on the temperature at mixing (addition), dissolution, or dispersion of the surfactant. Similar to the case of mixing, dissolution, or dispersion of the aforementioned hydrocarbonization agent, the temperature may be appropriately adjusted (to, for example, room temperature (ambient temperature) to 50° C.) depending on the solubility or dispersibility of the surfactant.

When a base is used, no particular limitation is imposed on the order of mixing (addition), dissolution, and dispersion of the base. Specifically, the base may be mixed with and dissolved or dispersed in a solvent, water, a buffer, a water-soluble organic solvent, or a mixed solvent of water and a water-soluble organic solvent during mixing of the aforementioned hydrocarbonization agent. Alternatively, the base may be added to and dissolved or dispersed in such a solvent before or after mixing of the hydrocarbonization agent.

No particular limitation is imposed on the temperature at mixing (addition), dissolution, or dispersion of the base. Similar to the case of mixing, dissolution, or dispersion of the aforementioned hydrocarbonization agent, the temperature may be appropriately adjusted (to, for example, room temperature (ambient temperature) to 50° C.) depending on the solubility of the base used.

(5) Step T of Mixing Solution or Dispersion of Hydrocarbonization Agent with Dihalogenated Isocyanuric Acid Derivative Serving as Starting Material The step T involves mixing the solution (dispersion) or aqueous solution (aqueous dispersion) of the hydrocarbonization agent provided in the step S with at least one dihalogenated isocyanuric acid derivative selected from the group consisting of a dihalogenated isocyanuric acid, a dihalogenated isocyanuric acid salt, and a dihalogenated isocyanuric acid salt hydrate.

The definitions, specific examples, and other conditions (e.g., amount to be used) of the dihalogenated isocyanuric acid derivative are the same as those described above.

The aforementioned dihalogenated isocyanuric acid derivative may be mixed in the form of a solid. Alternatively, the dihalogenated isocyanuric acid derivative may optionally be dissolved or dispersed in a solvent, and may be used in the form of a solution or a dispersion. When the dihalogenated isocyanuric acid derivative is mixed in the form of a solid, the entirety of the derivative may be mixed at one time, or the derivative may be divided into small portions and mixed little by little. When the dihalogenated isocyanuric acid derivative in the form of a solid is added to and mixed with the aforementioned solution or dispersion in the absence of a base, an N-(hydrocarbon)isocyanuric acid can be more selectively produced.

The solution (dispersion) or aqueous solution (aqueous dispersion) provided in the aforementioned step S is mixed with the dihalogenated isocyanuric acid derivative generally after the step S of providing the solution (dispersion) or aqueous solution (aqueous dispersion) of the hydrocarbonization agent.

No limitation is imposed on this mixing method, so long as the solution (dispersion) or aqueous solution (aqueous dispersion) provided in the aforementioned step S is mixed with the dihalogenated isocyanuric acid derivative.

Next will be described a method for mixing the solution (dispersion) or aqueous solution (aqueous dispersion) provided in the step S with the dihalogenated isocyanuric acid derivative.

Firstly, the dihalogenated isocyanuric acid derivative is added to the solution (dispersion) or aqueous solution (aqueous dispersion) provided in the step S without any treatment (e.g., without temperature adjustment). In this case, the solution (dispersion) or aqueous solution (aqueous dispersion) provided in the step S may be added to the dihalogenated isocyanuric acid derivative (without, for example, temperature adjustment).

After completion of this addition, the reaction of producing an N-(hydrocarbon)isocyanuric acid proceeds in the reaction system. In this case, when the aforementioned base is absent in the reaction system, an N-mono(hydrocarbon)isocyanuric acid is selectively produced, whereas when the aforementioned base is present in the reaction system, an N-di(hydrocarbon)isocyanuric acid is selectively produced. After completion of the addition, the production of an N-(hydrocarbon)isocyanuric acid can be promoted by stirring the reaction system.

After completion of the addition, the reaction temperature (the temperature in the reaction system) can be maintained at ambient temperature (20° C.±15° C.) following the aforementioned step S, and may be appropriately adjusted (to, for example, room temperature (ambient temperature) to 50° C.) in consideration of, for example, the degree of progress of the reaction or the recovery procedure after production of an N-(hydrocarbon)isocyanuric acid. The reaction of production of an N-(hydrocarbon)isocyanuric acid seems to proceed relatively easily even at room temperature (ambient temperature), and thus the reaction at room temperature (ambient temperature) is advantageous from the industrial viewpoint.

No particular limitation is imposed on the reaction time, so long as the effects of the present invention are not impaired. The reaction time may vary depending on the type of the hydrocarbonization agent to be used, the presence or absence of a surfactant, and the type of the surfactant, and the reaction time is, for example, 0.1 hours to 10 hours.

The purification operation after the reaction is performed as described above.

EXAMPLES

The present invention will next be described in more detail by way of Examples, but the present invention should not be construed as being limited to the following Examples.

In the Examples, the following apparatuses and conditions were used for preparation of samples and analysis of physical properties.

(1) HPLC: LC-2010A HT System, available from SHIMADZU CORPORATION

Column: HyperCarb (Thermo), 5 μm, 4.6×100 mm
Oven: 40° C.
Detector: UV 210 nm
Flow rate: 1.0 mL/minute
Eluent and Conditions: liquid A=acetonitrile for HPLC, liquid B=0.1% by mass aqueous phosphoric acid solution
0 min to 8 min liquid B 90%→20 min liquid B 5% (gradation)
20 min to 25 min liquid B 5% (continuation)
25 min liquid B 5%→25.1 min liquid B 90% (gradation)
25.1 min to 30 min liquid B 90% (continuation)
Internal standard substance for quantitative analysis: p-xylene Preparation of calibration curve of monomethylisocyanuric acid: Firstly, 100 mg of standard monomethylisocyanuric acid was placed in a 50 mL measuring flask, and the flask was charged with acetonitrile to a predetermined volume. Subsequently, the resultant solution was removed from the flask with 5 mL, 10 mL, and 15 mL transfer pipettes, and each portion of the solution was added to a 50 mL measuring flask.

Separately, 0.50 g of p-xylene was placed in a 500 mL measuring flask, and the flask was charged with acetonitrile to a predetermined volume, to thereby prepare an internal standard solution. The resultant solution was removed from the flask with a 5 mL transfer pipette, and then added to each 50 mL measuring flask containing the above-prepared standard monomethylisocyanuric acid solution. The flask was charged with acetonitrile to a predetermined volume.

The thus-prepared three standard solutions were analyzed by HPLC, to thereby prepare a three-point internal standard calibration curve. The calibration curve was used for quantification of monomethylisocyanuric acid.

Quantification of dimethylisocyanuric acid: The molar sensitivity ratio of standard dimethylisocyanuric acid to standard monomethylisocyanuric acid was determined to be 1.93 under the present analytical conditions. Dimethylisocyanuric acid was quantified by the following formula using the internal standard quantitative value of monomethylisocyanuric acid and the molar sensitivity ratio of dimethylisocyanuric acid.

Quantitative value of dimethylisocyanuric acid=(the peak area of dimethylisocyanuric acid/the peak area of monomethylisocyanuric acid)×the internal standard quantitative value of monomethylisocyanuric acid/the molar sensitivity ratio (1.93)

Quantification of trimethylisocyanuric acid: The molar sensitivity ratio of standard trimethylisocyanuric acid to standard monomethylisocyanuric acid was determined to be 2.97 under the present analytical conditions. Trimethylisocyanuric acid was quantified by the following formula using the internal standard quantitative value of monomethylisocyanuric acid and the molar sensitivity ratio of trimethylisocyanuric acid.

Quantitative value of trimethylisocyanuric acid=(the peak area of trimethylisocyanuric acid/the peak area of monomethylisocyanuric acid)×the internal standard quantitative value of monomethylisocyanuric acid/the molar sensitivity ratio (2.97)

Retention time: trichloroisocyanuric acid: 1.5 min, sodium dichloroisocyanurate: 2.3 min, isocyanuric acid: 2.3 min, monomethylisocyanuric acid: 3.5 min, dimethylisocyanuric acid: 7.0 min, trimethylisocyanuric acid: 12.2 min, p-xylene: 16.0 min, monoethylisocyanuric acid: 3.7 min, diethylisocyanuric acid: 7.4 min, triethylisocyanuric acid: 12.3 min (2) $^1$H-NMR: JNM-ECA500, available from JEOL Ltd.
Monomethylisocyanuric acid $^1$H-HMR (500 MHz, DMSO-$d_6$, δ ppm): 11.4 (2H, d, J=4.0 Hz) 3.04 (3H, s).
Dimethylisocyanuric acid $^1$H-HMR (500 MHz, DMSO-$d_6$, δ ppm): 11.6 (1H, s), 3.10 (6H, s).
Trimethylisocyanuric acid $^1$H-HMR (500 MHz, DMSO-$d_6$, δ ppm): 3.16 (9H, s).

[Example 1] Reaction in Water

A glass-made reaction container was charged with 5.23 g of sodium dichloroisocyanurate (trade name: HILITE 60G, available from Nissan Chemical Corporation) and 30.0 g of water, and the resultant mixture was stirred at 20° C. for homogeneous dissolution. Thereafter, 6.00 g of dimethyl sulfate (available from Tokyo Chemical Industry Co., Ltd.) was added dropwise to the resultant solution. The resultant mixture was stirred at 20° C., and then solids of monomethylisocyanuric acid (MMe-ICA) and dimethylisocyanuric acid (DMe-ICA) were precipitated over time. The mixture containing the solids was stirred for six hours.

The reaction product was diluted with acetonitrile for HPLC (available from KANTO CHEMICAL CO., INC.) and pure water in a measuring flask, and the diluted product was sampled. p-Xylene (internal standard substance) was added to the sample, and quantitative analysis was performed by HPLC.

As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 87.0%, 3.7%, and 0.0%, respectively. The results are shown in Table 1.

[Example 2] Reaction in Water Using Surfactant (Phase Transfer Catalyst)

A glass-made reaction container was charged with 5.23 g of sodium dichloroisocyanurate (trade name: HILITE 60G, available from Nissan Chemical Corporation) and 30.0 g of water, and the resultant mixture was stirred at 20° C. for homogeneous dissolution. Thereafter, 0.09 g of tetramethylammonium chloride (available from Tokyo Chemical Industry Co., Ltd.) was added to the resultant solution, and then 6.00 g of dimethyl sulfate (available from Tokyo Chemical Industry Co., Ltd.) was added dropwise to the resultant solution. The resultant mixture was stirred at 20° C., and then solids of monomethylisocyanuric acid (MMe-ICA) and dimethylisocyanuric acid (DMe-ICA) were precipitated over time. The mixture containing the solids was stirred for two hours.

The quantitative analysis was performed in the same manner as in Example 1. As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 80.4%, 3.4%, and 0.0%, respectively. The results are shown in Table 1.

[Example 3] Reaction in Water

The reaction and the quantitative analysis were performed in the same manner as in Example 1, except that the amount of dimethyl sulfate was changed to 1.48 g, and the stirring time was changed from six hours to four hours.

As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 42.5%, 2.1%, and 0.0%, respectively. The results are shown in Table 1.

[Example 4] Reaction in Water

The reaction and the quantitative analysis were performed in the same manner as in Example 3, except that the amount of dimethyl sulfate was changed to 2.97 g.

As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 77.8%, 4.0%, and 0.0%, respectively. The results are shown in Table 1.

[Example 5] Reaction in Water

The reaction and the quantitative analysis were performed in the same manner as in Example 3, except that the amount of dimethyl sulfate was changed to 4.45 g.

As a result, the quantitative yields (with reference to sodium dichloroisocyanurate) of monomethylisocyanuric acid (MNIe-ICA), dimethylisocyanuric acid (DMe-ICA), and trimethylisocyanuric acid (TMe-ICA) were 80.8%, 3.8%, and 0.0%, respectively. The results are shown in Table 1.

[Example 6] Reaction in Water (Containing Base)

A glass-made reaction container was charged with 5.23 g of sodium dichloroisocyanurate (trade name: HILITE 60G, available from Nissan Chemical Corporation), 0.94 g of sodium hydroxide (special grade, available from KANTO CHEMICAL CO., INC.), and 30.0 g of water, and the resultant mixture was stirred at 20° C. for homogeneous dissolution. Thereafter, 6.00 g of dimethyl sulfate (available from Tokyo Chemical Industry Co., Ltd.) was added dropwise to the resultant solution. The resultant mixture was stirred at 20° C., and then solids of monomethylisocyanuric acid (MMe-ICA) and dimethylisocyanuric acid (DMe-ICA) were precipitated over time. The mixture containing the solids was stirred for two hours.

The quantitative analysis was performed in the same manner as in Example 1. As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 43.7%, 32.3%, and 0.3%, respectively. The results are shown in Table 1.

[Example 7] Reaction in Water (Containing Base)

The reaction and the quantitative analysis were performed in the same manner as in Example 6, except that the amount of sodium hydroxide was changed to 1.88 g.

As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 14.1%, 41.3%, and 5.8%, respectively. The results are shown in Table 1.

[Example 8] Reaction in Water (Use of Sodium Dichloroisocyanurate Hydrate)

A glass-made reaction container was charged with 6.10 g of sodium dichloroisocyanurate dihydrate (trade name: HILITE 55G, available from Nissan Chemical Corporation) and 30.0 g of water, and the resultant mixture was stirred at 20° C. for homogeneous dissolution. Thereafter, 4.51 g of dimethyl sulfate (available from Tokyo Chemical Industry Co., Ltd.) was added dropwise to the resultant solution. The resultant mixture was stirred at 20° C., and then solids of monomethylisocyanuric acid (MMe-ICA) and dimethylisocyanuric acid (DMe-ICA) were precipitated over time. The mixture containing the solids was stirred for six hours.

The quantitative analysis was performed in the same manner as in Example 1. As a result, the quantitative yields (with reference to sodium dichloroisocyanurate dihydrate) of monomethylisocyanuric acid (MIVIe-ICA), dimethylisocyanuric acid (DMe-ICA), and trimethylisocyanuric acid (TMe-ICA) were 82.8%, 3.2%, and 0.0%, respectively. The results are shown in Table 1.

[Example 9] Reaction in Water (Use of Sodium Dichloroisocyanurate Hydrate)

The reaction and the quantitative analysis were performed in the same manner as in Example 8, except that the amount of dimethyl sulfate was changed to 6.01 g.

As a result, the quantitative yields (with reference to sodium dichloroisocyanurate dihydrate) of monomethylisocyanuric acid (MIVIe-ICA), dimethylisocyanuric acid (DMe-ICA), and trimethylisocyanuric acid (TMe-ICA) were 79.4%, 2.9%, and 0.0%, respectively. The results are shown in Table 1.

TABLE 1

| | Quantitative yield with reference to sodium dichloroisocyanurate or sodium dichloroisocyanurate dihydrate | | |
|---|---|---|---|
| | MMe-ICA | DMe-ICA | TMe-ICA |
| Example 1 | 87.0% | 3.7% | 0.0% |
| Example 2 | 80.4% | 3.4% | 0.0% |
| Example 3 | 42.5% | 2.1% | 0.0% |
| Example 4 | 77.8% | 4.0% | 0.0% |
| Example 5 | 80.8% | 3.8% | 0.0% |
| Example 6 | 43.7% | 32.3% | 0.3% |
| Example 7 | 14.1% | 41.3% | 5.8% |
| Example 8 | 82.8% | 3.2% | 0.0% |
| Example 9 | 79.4% | 2.9% | 0.0% |

The results shown in Table 1 indicated that the production method of the present invention can selectively produce an N-mono(hydrocarbon)isocyanuric acid of interest (i.e., mono-substituted product of isocyanuric acid) in one pot at high production efficiency (Examples 1 to 5 and Examples 8 and 9).

The results also indicated that the presence of a base enables production of an N-di(hydrocarbon)isocyanuric acid (i.e., di-substituted product) at high yield, and adjustment of the amount of a base leads to more selective production of the di-substituted product (Examples 6 and 7).

[Example 10] Reaction in Buffer (Control of pH During Reaction)

The reaction and the quantitative analysis were performed in the same manner as in Example 1, except that water was replaced with 10 mM buffer having a pH adjusted to 7.0 (ammonium acetate (special grade, available from KANTO CHEMICAL CO., INC., ammonium formate (Cica first grade, available from KANTO CHEMICAL CO., INC.), aqueous solution).

As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 80.3%, 3.6%, and 0.0%, respectively. The results are shown in Table 2.

[Example 11] Reaction in Water (Reaction Temperature)

The reaction and the quantitative analysis were performed in the same manner as in Example 1, except that the reaction temperature was changed to 10° C., and the reaction time was changed to seven hours.

As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 85.2%, 2.8%, and 0.1%, respectively. The results are shown in Table 2.

[Example 12] Reaction in Water (Reaction Temperature)

The reaction and the quantitative analysis were performed in the same manner as in Example 1, except that the reaction temperature was changed to 30° C., and the reaction time was changed to three hours.

As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 78.4%, 2.6%, and 0.1%, respectively. The results are shown in Table 2.

[Example 13] Reaction in Water (Reaction Temperature)

The reaction and the quantitative analysis were performed in the same manner as in Example 12, except that the reaction temperature was changed to 40° C.

As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 77.3%, 2.5%, and 0.1%, respectively. The results are shown in Table 2.

[Example 14] Reaction in Water (Amount of Water, Reaction Temperature)

The reaction and the quantitative analysis were performed in the same manner as in Example 13, except that the amount of water was changed to 60.6 g.

As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 68.4%, 1.7%, and 0.1%, respectively. The results are shown in Table 2.

[Example 15] Reaction in Water (Amount of Water)

The reaction and the quantitative analysis were performed in the same manner as in Example 14, except that the reaction temperature was changed to 20° C.

As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 76.7%, 1.9%, and 0.1%, respectively. The results are shown in Table 2.

[Example 16] Reaction in Water (Amount of Water)

The reaction and the quantitative analysis were performed in the same manner as in Example 15, except that the amount of water was changed to 45.5 g.

As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 78.2%, 2.2%, and 0.1%, respectively. The results are shown in Table 2.

[Example 17] Reaction in Water (Dropwise Addition Time)

The reaction and the quantitative analysis were performed in the same manner as in Example 1, except that the dropwise addition time of dimethyl sulfate was prolonged to one hour, and the reaction time was changed to 2.5 hours.

As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 78.2%, 3.1%, and 0.1%, respectively. The results are shown in Table 2.

[Example 18] Reaction in Water (Dropwise Addition Time)

The reaction and the quantitative analysis were performed in the same manner as in Example 1, except that the dropwise addition time of dimethyl sulfate was prolonged to two hours, and the reaction time was changed to 1.5 hours.

As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 76.7%, 3.2%, and 0.1%, respectively. The results are shown in Table 2.

[Example 19] Reaction in Water (Addition of Sodium Dichloroisocyanurate)

A glass-made reaction container was charged with 6.00 g of dimethyl sulfate (available from Tokyo Chemical Industry Co., Ltd.) and 30.0 g of water, and the resultant mixture was stirred at 20° C. for dispersion. Thereafter, 5.28 g of sodium dichloroisocyanurate (trade name: HILITE 60G, available from Nissan Chemical Corporation) was added in a divided manner to the resultant dispersion over one hour. The resultant mixture was stirred at 20° C., and then solids of monomethylisocyanuric acid (MMe-ICA) and dimethylisocyanuric acid (DMe-ICA) were precipitated over time. The mixture containing the solids was stirred for 2.5 hours.

The quantitative analysis was performed in the same manner as in Example 1. As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 78.4%, 1.6%, and 0.1%, respectively. The results are shown in Table 2.

[Example 20] Reaction in Water (Addition of Sodium Dichloroisocyanurate)

The reaction and the quantitative analysis were performed in the same manner as in Example 19, except that the addition time of sodium dichloroisocyanurate was changed to two hours, and the reaction time was changed to 1.5 hours.

As a result, the quantitative yields (with reference to sodium dichloroisocyanurate) of monomethylisocyanuric acid (MMe-ICA), dimethylisocyanuric acid (DMe-ICA), and trimethylisocyanuric acid (TMe-ICA) were 77.3%, 1.3%, and 0.1%, respectively. The results are shown in Table 2.

TABLE 2

Quantitative yield with reference to sodium dichloroisocyanurate

|  | MMe-ICA | DMe-ICA | TMe-ICA |
|---|---|---|---|
| Example 10 | 80.3% | 3.6% | 0.0% |
| Example 11 | 85.2% | 2.8% | 0.1% |
| Example 12 | 78.4% | 2.6% | 0.1% |
| Example 13 | 77.3% | 2.5% | 0.1% |
| Example 14 | 68.4% | 1.7% | 0.1% |
| Example 15 | 76.7% | 1.9% | 0.1% |
| Example 16 | 78.2% | 2.2% | 0.1% |
| Example 17 | 78.2% | 3.1% | 0.1% |
| Example 18 | 76.7% | 3.2% | 0.1% |
| Example 19 | 78.4% | 1.6% | 0.1% |
| Example 20 | 77.3% | 1.3% | 0.1% |

The results shown in Table 2 indicated that the production method of the present invention can selectively produce an N-mono(hydrocarbon)isocyanuric acid of interest (i.e., mono-substituted product of isocyanuric acid) in one pot at high production efficiency (Examples 10 to 20).

[Example 21] Generation of Sodium Dichloroisocyanurate in Reaction System

A glass-made reaction container was charged with 3.07 g of isocyanuric acid (trade name: CA-P, available from Nissan Chemical Corporation) and 35.90 g of aqueous sodium hypochlorite solution (Cica first grade, available from KANTO CHEMICAL CO., INC.), and the resultant mixture was stirred at 40° C. for homogeneous dissolution, to thereby generate sodium dichloroisocyanurate in the reaction system. Thereafter, the resultant solution was cooled to 20° C., and 6.00 g of dimethyl sulfate (available from Tokyo Chemical Industry Co., Ltd.) was added dropwise to the solution. The resultant mixture was stirred at 20° C. for six hours.

The quantitative analysis was performed in the same manner as in Example 1. As a result, the quantitative yields (with reference to isocyanuric acid) of monomethylisocyanuric acid (MMe-ICA), dimethylisocyanuric acid (DMe-ICA), and trimethylisocyanuric acid (TMe-ICA) were 27.2%, 7.9%, and 0.2%, respectively. The results are shown in Table 3.

TABLE 3

Quantitative yield with reference to isocyanuric acid

|  | MMe-ICA | DMe-ICA | TMe-ICA |
|---|---|---|---|
| Example 21 | 27.2% | 7.9% | 0.2% |

The results shown in Table 3 indicated that the production method of the present invention can selectively produce an N-mono(hydrocarbon)isocyanuric acid of interest (i.e., mono-substituted product of isocyanuric acid) in one pot.

[Examples 22 to 26] Reaction in Organic Solvent

A glass-made reaction container was charged with 5.28 g of sodium dichloroisocyanurate (trade name: HILITE 60G, available from Nissan Chemical Corporation) and 30.0 g of an organic solvent or a mixed solvent of an organic solvent and water shown in Table 4, and the resultant mixture was stirred at 20° C. Thereafter, 6.00 g of dimethyl sulfate (available from Tokyo Chemical Industry Co., Ltd.) was added dropwise to the resultant solution. The resultant mixture was stirred for six hours.

The reaction product was diluted with acetonitrile for HPLC (available from KANTO CHEMICAL CO., INC.) and pure water in a measuring flask, and the diluted product was sampled. p-Xylene (internal standard substance) was added to the sample, and quantitative analysis was performed by HPLC.

The results are shown in Table 4.

TABLE 4

Quantitative yield with reference to sodium dichloroisocyanurate

|  | Solvent | MMe-ICA | DMe-ICA | TMe-ICA |
|---|---|---|---|---|
| Example 22 | DMF | 83.5% | 5.7% | 5.3% |
| Example 23 | DMF/water = 1:1 | 84.1% | 3.7% | 0.2% |
| Example 24 | Acetonitrile/water = 1:1 | 92.6% | 3.5% | 0.2% |
| Example 25 | NMP/water = 1:1 | 89.4% | 4.4% | 0.2% |
| Example 26 | PGMEA/water = 1:1 | 86.3% | 5.0% | 0.2% |

The results shown in Table 4 indicated that the production method of the present invention can selectively produce an N-mono(hydrocarbon)isocyanuric acid of interest (i.e., mono-substituted product of isocyanuric acid) by using various solvents in one pot at high production efficiency.

[Example 27] Reaction in Water (Hydrocarbonization Agent)

A glass-made reaction container was charged with 5.28 g of sodium dichloroisocyanurate (trade name: HILITE 60G, available from Nissan Chemical Corporation), 0.05 g of tetra-n-butylammonium bromide (available from Tokyo Chemical Industry Co., Ltd.), and 30.0 g of water, and the resultant mixture was stirred at 20° C. for homogeneous dissolution. Thereafter, 5.32 g of methyl iodide (available from Tokyo Chemical Industry Co., Ltd.) was added dropwise to the resultant solution. The resultant mixture was stirred at 20° C., and then solids of monomethylisocyanuric acid (MMe-ICA) and dimethylisocyanuric acid (DMe-ICA) were precipitated over time. The mixture containing the solids was stirred for six hours.

The quantitative analysis was performed in the same manner as in Example 1. As a result, the quantitative yields (with reference to sodium dichloroisocyanurate) of monomethylisocyanuric acid (MIVIe-ICA), dimethylisocyanuric acid (DMe-ICA), and trimethylisocyanuric acid (TMe-ICA) were 9.0%, 0.0%, and 0.0%, respectively. The results are shown in Table 5.

[Example 28] Reaction in Organic Solvent (Hydrocarbonization Agent)

A glass-made reaction container was charged with 5.28 g of sodium dichloroisocyanurate (trade name: HILITE 60G, available from Nissan Chemical Corporation) and 30.0 g of dimethylformamide, and the resultant mixture was stirred at 20° C. for homogeneous dissolution. Thereafter, 7.33 g of diethyl sulfate (available from Tokyo Chemical Industry Co., Ltd.) was added dropwise to the resultant solution. The resultant mixture was stirred at 20° C. for six hours.

The quantitative analysis was performed in the same manner as in Example 1. As a result, the quantitative yields (with reference to sodium dichloroisocyanurate) of monoethylisocyanuric acid (MEt-ICA), diethylisocyanuric acid (DEt-ICA), and triethylisocyanuric acid (TEt-ICA) were 90.8%, 0.4%, and 0.0%, respectively. The results are shown in Table 5.

TABLE 5

| Quantitative yield with reference to sodium dichloroisocyanurate | | | | |
| --- | --- | --- | --- | --- |
| | Hydrocarbonization agent | MMe-ICA | DMe-ICA | TMe-ICA |
| Example 27 | MeI | 9.0% | 0.0% | 0.0% |
| | Hydrocarbonization agent | MEt-ICA | DEt-ICA | TEt-ICA |
| Example 28 | Et$_2$SO$_4$ | 90.8% | 0.4% | 0.0% |

The results shown in Table 5 indicated that the production method of the present invention can selectively produce an N-mono(hydrocarbon)isocyanuric acid of interest (i.e., mono-substituted product of isocyanuric acid) by using various hydrocarbonization agents in one pot.

[Example 29] Purification of Monomethylisocyanuric acid (MMe-ICA)

The reaction was performed by the method of Example 11, and then filtration was performed at ambient temperature, to thereby recover 4.65 g of a wet product containing MMe-ICA. The wet product was placed in a glass-made reaction container, and 3.50 g of methanol (special grade, available from KANTO CHEMICAL CO., INC.) and 28.0 g of water were added to the container, followed by heating to 95° C. Subsequently, 5.0 g of toluene (special grade, available from KANTO CHEMICAL CO., INC.) was added to the resultant mixture for phase separation and recovery of the aqueous phase. This operation was repeated twice. Thereafter, the aqueous phase was cooled to 5° C. and stirred for one hour, and 3.08 g of a precipitated wet product containing a large amount of MMe-ICA was recovered through filtration. Subsequently, 2.46 g of the wet product was placed in a glass-made reaction container, and 13.8 g of methanol was added to the container, followed by heating to 65° C. Thereafter, the resultant mixture was cooled to 5° C. and stirred for one hour, and 2.05 g of a precipitated wet product containing a larger amount of MMe-ICA was recovered through filtration. The resultant wet product was dried under reduced pressure, to thereby yield 1.39 g of an MMe-ICA crystal. The MMe-ICA crystal was diluted with acetonitrile for HPLC in a measuring flask, and relative area (%) was analyzed by HPLC. The relative areas (%) of monomethylisocyanuric acid (MMe-ICA), dimethylisocyanuric acid (DMe-ICA), trimethylisocyanuric acid (TMe-ICA), and others were 98.5%, 0.5%, 0.7%, and 0.3%, respectively.

[Example 30] Purification of Dimethylisocyanuric Acid (DMe-ICA)

The reaction was performed by the method of Example 7, and then the resultant reaction mixture was cooled to 10° C. and subjected to filtration, to thereby recover 5.03 g of a wet product containing DMe-ICA. The wet product was placed in a glass-made reaction container, and 20 g of water was added to the container, followed by heating to 50° C. Thereafter, the resultant product was cooled to 10° C., and 4.76 g of a precipitated wet product containing a larger amount of DMe-ICA was recovered through filtration. The same operation was repeated again, and 4.61 g of a wet product containing a larger amount of DMe-ICA was recovered through filtration. Subsequently, the wet product was placed in a glass-made reaction container, and 15 g of methanol (special grade, available from KANTO CHEMICAL CO., INC.) was added to the container, followed by heating to 60° C. Thereafter, the resultant mixture was cooled to 10° C., and 2.12 g of a precipitated wet product containing a larger amount of DMe-ICA was recovered through filtration. The resultant wet product was dried under reduced pressure, to thereby yield 2.03 g of a DMe-ICA crystal. The DMe-ICA crystal was diluted with acetonitrile for HPLC in a measuring flask, and relative area (%) was analyzed by HPLC. The relative areas (%) of monomethylisocyanuric acid (MMe-ICA), dimethylisocyanuric acid (DMe-ICA), and trimethylisocyanuric acid (TMe-ICA) were 6.9%, 92.7%, and 0.4%, respectively.

[Comparative Example 1] Reaction in Water Using Isocyanuric Acid (Containing Base)

A glass-made reaction container was charged with 3.07 g of isocyanuric acid (trade name: CA-P, available from Nissan Chemical Corporation), 0.95 g of sodium hydroxide (special grade, available from KANTO CHEMICAL CO., INC.), and 30.0 g of water, and the resultant mixture was stirred at 20° C. However, homogeneous dissolution failed to be achieved. Thereafter, 6.00 g of dimethyl sulfate (available from Tokyo Chemical Industry Co., Ltd.) was added dropwise to the resultant slurry. The resultant mixture was stirred at 20° C. for two hours.

The quantitative analysis was performed in the same manner as in Example 1. As a result, the quantitative yields (with reference to isocyanuric acid) of monomethylisocyanuric acid (MMe-ICA), dimethylisocyanuric acid (DMe-ICA), and trimethylisocyanuric acid (TMe-ICA) were 11.2%, 12.1%, and 0.4%, respectively. The results are shown in Table 6.

[Comparative Example 2] Reaction in Water Using Isocyanuric Acid (Containing Base)

The reaction and the quantitative analysis were performed in the same manner as in Comparative Example 1, except that the amount of sodium hydroxide was changed to 1.90 g.

As a result, the quantitative yields (with reference to isocyanuric acid) of monomethylisocyanuric acid (MMe-ICA), dimethylisocyanuric acid (DMe-ICA), and trimethylisocyanuric acid (TMe-ICA) were 13.9%, 25.9%, and 0.0%, respectively. The results are shown in Table 6.

TABLE 6

| Quantitative yield with reference to isocyanuric acid | | | |
| --- | --- | --- | --- |
| | MMe-ICA | DMe-ICA | TMe-ICA |
| Comparative Example 1 | 11.2% | 12.1% | 0.4% |
| Comparative Example 2 | 13.9% | 25.9% | 0.0% |

As shown in Table 6, when isocyanuric acid was used as a starting material, the yield of N-di(hydrocarbon)isocyanuric acid (i.e., di-substituted product) was improved by increasing the amount of the base. However, the selectivity of the target product was impaired as compared with the case of the method of the present invention shown in Table 1.

The invention claimed is:

1. A method for producing an N-(hydrocarbon)isocyanuric acid, the method comprising:
a step N of reacting, in a solvent, at least one dihalogenated isocyanuric acid derivative selected from the group consisting of a dihalogenated isocyanuric acid, a dihalogenated isocyanuric acid salt, and a dihalogenated isocyanuric acid salt hydrate with at least one hydrocarbonization agent selected from the group consisting of a halogenated hydrocarbon compound, a pseudo-halogenated hydrocarbon compound, and a dialkyl sulfate compound.

2. The method for producing an N-(hydrocarbon)isocyanuric acid according to claim 1, wherein:
the step N comprises a step X of providing a solution or dispersion of at least one dihalogenated isocyanuric acid derivative selected from the group consisting of a dihalogenated isocyanuric acid, a dihalogenated isocyanuric acid salt, and a dihalogenated isocyanuric acid salt hydrate, and
a step Y of mixing the solution or dispersion of the dihalogenated isocyanuric acid derivative with at least one hydrocarbonization agent selected from the group consisting of a halogenated hydrocarbon compound, a pseudo-halogenated hydrocarbon compound, and a dialkyl sulfate compound; or comprises
a step S of providing a solution or dispersion of at least one hydrocarbonization agent selected from the group consisting of a halogenated hydrocarbon compound, a pseudo-halogenated hydrocarbon compound, and a dialkyl sulfate compound, and
a step T of mixing the solution or dispersion of the hydrocarbonization agent with at least one dihalogenated isocyanuric acid derivative selected from the group consisting of a dihalogenated isocyanuric acid, a dihalogenated isocyanuric acid salt, and a dihalogenated isocyanuric acid salt hydrate.

3. The method for producing an N-(hydrocarbon)isocyanuric acid according to claim 2, wherein the solution or dispersion of the dihalogenated isocyanuric acid derivative is an aqueous solution or an aqueous dispersion.

4. The method for producing an N-(hydrocarbon)isocyanuric acid according to claim 3, wherein the aqueous solution or aqueous dispersion of the dihalogenated isocyanuric acid derivative contains water at a mixing ratio (by mass) of the water to the solvent of 0.1:99.9 to 99.9:0.1.

5. The method for producing an N-(hydrocarbon)isocyanuric acid according to claim 2, wherein the step Y is a step of mixing the solution or dispersion of the dihalogenated isocyanuric acid derivative with at least one hydrocarbonization agent selected from the group consisting of a halogenated hydrocarbon compound, a pseudo-halogenated hydrocarbon compound, and a dialkyl sulfate compound, and with a surfactant.

6. The method for producing an N-(hydrocarbon)isocyanuric acid according to claim 5, wherein the surfactant contains at least one selected from the group consisting of a quaternary ammonium salt, a crown ether, and an alkylbenzenesulfonic acid salt.

7. The method for producing an N-(hydrocarbon)isocyanuric acid according to claim 2, wherein the step X is a step of providing a solution or dispersion containing at least one dihalogenated isocyanuric acid derivative selected from the group consisting of a dihalogenated isocyanuric acid, a dihalogenated isocyanuric acid salt, and a dihalogenated isocyanuric acid salt hydrate, and a base.

8. The method for producing an N-(hydrocarbon)isocyanuric acid according to claim 7, wherein the base contains an inorganic base.

9. The method for producing an N-(hydrocarbon)isocyanuric acid according to claim 2, wherein the solution or dispersion of the hydrocarbonization agent is an aqueous solution or an aqueous dispersion.

10. The method for producing an N-(hydrocarbon)isocyanuric acid according to claim 9, wherein the aqueous solution or aqueous dispersion of the hydrocarbonization agent contains water at a mixing ratio (by mass) of the water to the solvent of 0.1:99.9 to 99.9:0.1.

11. The method for producing an N-(hydrocarbon)isocyanuric acid according to claim 2, wherein the step S is a step of providing a solution or dispersion containing at least one hydrocarbonization agent selected from the group consisting of a halogenated hydrocarbon compound, a pseudo-halogenated hydrocarbon compound, and a dialkyl sulfate compound, and a surfactant.

12. The method for producing an N-(hydrocarbon)isocyanuric acid according to claim 11, wherein the surfactant contains at least one selected from the group consisting of a quaternary ammonium salt, a crown ether, and an alkylbenzenesulfonic acid salt.

13. The method for producing an N-(hydrocarbon)isocyanuric acid according to claim 2, wherein the step S is a step of providing a solution or dispersion containing at least one hydrocarbonization agent selected from the group consisting of a halogenated hydrocarbon compound, a pseudo-halogenated hydrocarbon compound, and a dialkyl sulfate compound, and a base.

14. The method for producing an N-(hydrocarbon)isocyanuric acid according to claim 13, wherein the base contains an inorganic base.

15. The method for producing an N-(hydrocarbon)isocyanuric acid according to claim 1, wherein the hydrocarbonization agent contains at least one selected from the group consisting of methyl p-toluenesulfonate, ethyl p-toluenesulfonate, methyl methanesulfonate, ethyl methanesulfonate, dimethyl sulfate, and diethyl sulfate.

16. The method for producing an N-(hydrocarbon)isocyanuric acid according to claim 15, wherein the hydrocarbonization agent contains at least one selected from the group consisting of dimethyl sulfate and diethyl sulfate.

17. The method for producing an N-(hydrocarbon)isocyanuric acid according to claim 1, wherein the dihalogenated isocyanuric acid derivative contains at least one selected from the group consisting of dichloroisocyanuric acid, sodium dichloroisocyanurate, and sodium dichloroisocyanurate dihydrate.

18. The method for producing an N-(hydrocarbon)isocyanuric acid according to claim 17, wherein the dihalogenated isocyanuric acid derivative contains sodium dichloroisocyanurate.

19. The method for producing an N-(hydrocarbon)isocyanuric acid according to claim 1, wherein the amount of the hydrocarbonization agent is 0.3 mole equivalent to 4.0 mole equivalent relative to 1 mole equivalent of the dihalogenated isocyanuric acid derivative.

20. The method for producing an N-(hydrocarbon)isocyanuric acid according to claim 1, wherein the amount of the dihalogenated isocyanuric acid derivative is 0.03 to 0.3 times by mass that of the solvent used.

* * * * *